US012692218B2

(12) United States Patent
Hattori et al.

(10) Patent No.: US 12,692,218 B2
(45) Date of Patent: Jul. 28, 2026

(54) RESIST MATERIAL AND PATTERN FORMING METHOD

(71) Applicant: Oji Holdings Corporation, Tokyo (JP)

(72) Inventors: Kimiko Hattori, Tokyo (JP); Kazuyo Morita, Tokyo (JP)

(73) Assignee: Oji Holdings Corporation, Tokyo (JP)

( * ) Notice: Subject to any disclaimer, the term of this patent is extended or adjusted under 35 U.S.C. 154(b) by 0 days.

(21) Appl. No.: 18/829,865

(22) Filed: Sep. 10, 2024

(65) Prior Publication Data

US 2025/0004376 A1 Jan. 2, 2025

Related U.S. Application Data

(63) Continuation of application No. 17/623,995, filed as application No. PCT/JP2020/025632 on Jun. 30, 2020, now Pat. No. 12,248,249.

(30) Foreign Application Priority Data

Jul. 2, 2019 (JP) ................................ 2019-123878

(51) Int. Cl.

| | |
|---|---|
| ***C07C 69/653*** | (2006.01) |
| ***C08F 220/22*** | (2006.01) |
| ***C08F 220/28*** | (2006.01) |
| ***G03F 7/039*** | (2006.01) |
| ***G03F 7/20*** | (2006.01) |

(52) U.S. Cl.

CPC .......... *C07C 69/653* (2013.01); *C08F 220/22* (2013.01); *C08F 220/283* (2020.02); *G03F 7/039* (2013.01); *G03F 7/2059* (2013.01)

(58) Field of Classification Search

CPC ....... C07C 69/653; G03F 7/0397; G03F 7/30; C08F 220/22; C08F 220/283

See application file for complete search history.

(56) References Cited

U.S. PATENT DOCUMENTS

| | | | | |
|---|---|---|---|---|
| 9,944,740 | B2 * | 4/2018 | Navale | ................ C08F 220/283 |
| 2010/0266966 | A1 | 10/2010 | Park | |
| 2012/0156595 | A1 | 6/2012 | Oh | |

FOREIGN PATENT DOCUMENTS

| | | | |
|---|---|---|---|
| JP | S60-117243 | A | 6/1985 |
| JP | S63-137227 | A | 6/1988 |

(Continued)

OTHER PUBLICATIONS

Office Action dated Nov. 21, 2024 issued in the corresponding Korean patent application No. 10-2022-7001577 with its English Machine Translation.

(Continued)

*Primary Examiner* — John S. Chu

(74) *Attorney, Agent, or Firm* — Troutman Pepper Locke LLP

(57) ABSTRACT

It is an object of the present invention to form a resist film that is highly sensitive and enables high-resolution patterning. The present invention relates to a resist material that comprises a polymer comprising a unit derived from a structure represented by the following formula (101). In the formula (101), $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent, and a plurality of $R^1$ may be the same or different. $R^{11}$ represents a hydrogen atom or an alkyl group optionally having a substituent. $R^2$ represents a hydrogen atom, an alkyl group, a fluorine atom, a chlorine atom, a bromine atom, or a halogenated alkyl group; and $Y^1$ represents a single bond or a linking group.

(Continued)

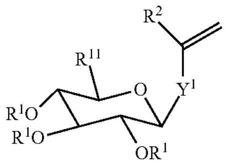

Formula (101)

3 Claims, 1 Drawing Sheet

(56) References Cited

FOREIGN PATENT DOCUMENTS

| | | | | |
|---|---|---|---|---|
| JP | H07-234511 | A | | 9/1995 |
| JP | 2012-113303 | A | | 6/2012 |
| JP | 2013-145255 | A | | 7/2013 |
| JP | 2021148831 | A | * | 9/2021 |
| TW | 201908350 | A | | 3/2019 |
| WO | 99/62964 | A1 | | 12/1999 |
| WO | 2017/199521 | A1 | | 11/2017 |
| WO | 2019/012716 | A1 | | 1/2019 |

OTHER PUBLICATIONS

International Search Report and Written Opinion issued in corresponding PCT/JP2020/025632 dated Aug. 18, 2020.

Japanese version of International Preliminary Report on Patentability of Chapter I with English version issued in corresponding PCT/JP2020/025632 dated Jan. 13, 2022.

Taiwanese Office Action dated May 28, 2021 with its English Translation issued in the corresponding Taiwanese patent application No. 109122186.

Taiwanese Office Action dated May 31, 2021 with its English Translation issued in the corresponding Taiwanese patent application No. 110116606.

* cited by examiner

RESIST MATERIAL AND PATTERN FORMING METHOD

TECHNICAL FIELD

The present invention relates to a resist material and a pattern forming method.

BACKGROUND ART

Electronic devices such as semiconductors are required to be highly integrated due to miniaturization. Regarding the patterns of semiconductor devices, For example, a lithography method using a photoresist is a processing method in which a photoresist pattern is obtained by forming a photoresist thin film is formed on a semiconductor substrate such as a silicon wafer, irradiating an actinic ray such as an ultraviolet ray through a mask pattern on which a pattern of a semiconductor device is drawn, and performing development, and then, fine irregularities corresponding to the pattern are formed on the substrate by etching the substrate with the obtained photoresist pattern as a protective film.

As resist materials that constitute resist films, polymers having various structures have been used depending on the intended uses thereof or required physical properties. For example, as a polymer used in a resist material, a polymer comprising a structural unit derived from (meth)acrylate has been known. Patent Documents 1 to 3 disclose studies regarding the use of a polymer formed by copolymerizing α-methylstyrene with methacrylic acid or methacrylic acid ester as a resist material.

In addition, Patent Document 4 discloses studies regarding the use of a polymer obtained by polymerizing an adamantyl methacrylate monomer with a t-butyl acrylate monomer as a radiation photosensitive material. Thus, two types of specific monomers are copolymerized with each other to obtain a resist material, and a resist film is formed from the obtained resist material.

PRIOR ART DOCUMENTS

Patent Documents

Patent Document 1: JP Patent Publication-A-60-117243 (1985)
Patent Document 2: JP Patent Publication-A-63-137227 (1988)
Patent Document 3: International Publication WO99/62964
Patent Document 4: JP Patent Publication-A-07-234511 (1995)

SUMMARY OF INVENTION

Object to Be Solved by the Invention

As described above, in a lithographic method using a photoresist, the formation of a fine pattern has been studied. In order to form such a fine pattern, it is necessary to pattern a resist film with high resolution, and thus, it has been desired to develop a resist material capable of forming a pattern with a high resolution.

On the other hand, in order to form a high-resolution pattern, the structure of a polymer used in a resist material needs to be studied, as appropriate. However, there is a case where the sensitivity of a resist material becomes poor depending on the type of a component that constitutes the polymer. In such a case, the irradiation amount of an electromagnetic wave per unit area, which is used upon patterning, is enhanced, so that the accuracy of patterning needs to be enhanced.

Hence, in order to solve the aforementioned problem of the prior art technique, the present inventors have conducted studies for the purpose of providing a resist material capable of forming a resist film that is highly sensitive and enables high-resolution patterning.

Means for Solving the Object

As a result of intensive studies conducted directed towards achieving the aforementioned object, the present inventors have found that a resist film that is highly sensitive and enables high-resolution patterning can be formed by using a monomer having a predetermined structure as a polymerized component of a polymer that constitutes a resist material.

Specifically, the present invention has the following configurations.

[1] A resist material that comprises a polymer comprising a unit derived from a structure represented by the following formula (101):

[Formula 1]

Formula (101)

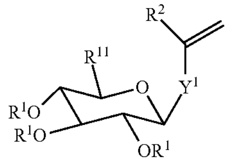

wherein $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent, and a plurality of $R^1$ may be the same or different; $R^{11}$ represents a hydrogen atom or an alkyl group optionally having a substituent; $R^2$ represents a hydrogen atom, an alkyl group, a fluorine atom, a chlorine atom, a bromine atom, or a halogenated alkyl group; and $Y^1$ represents a single bond or a linking group.

[2] A The resist material according to [1], wherein the polymer further comprises a unit derived from a structure represented by the following formula (102):

[Formula 2]

Formula (102)

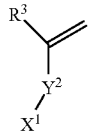

wherein $X^1$ represents an alkyl group optionally having a substituent, an acyl group optionally having a substituent, or an allyl group optionally having a substituent; $R^3$ represents a hydrogen atom, an alkyl group, a fluorine atom, a chlorine atom, a bromine atom, or a halogenated alkyl group; and $Y^2$ represents a single bond or a linking group.

[3] A The resist material according to [1] or [2], wherein the polymer further comprises a unit derived from a structure represented by the following formula (103):

[Formula 3]

Formula (103)

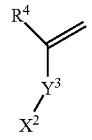

wherein $X^2$ represents an aryl group optionally having a substituent; $R^4$ represents a hydrogen atom, an alkyl group, a fluorine atom, a chlorine atom, a bromine atom, or a halogenated alkyl group; and $Y^3$ represents a single bond or a linking group.

[4] The resist material according to any one of [1] to [3], wherein, in the formula (101), $R^2$ is a fluorine atom, a chlorine atom, or a bromine atom.

[5] The resist material according to any one of [1] to [4], wherein, in the formula (101), $R^{11}$ is a hydrogen atom.

[6] The resist material according to any one of [2] to [5], wherein, in the formula (102), $R^3$ represents a fluorine atom, a chlorine atom, or a bromine atom.

[7] A resist film formed from the resist material according to any one of [1] to [6].

[8] A pattern forming method, comprising:

applying the resist material according to any one of [1] to [6] onto a substrate to form a resist film, exposing, and developing.

[9] The pattern forming method according to [8], further comprising:

introduction a metal before the developing.

[10] A The pattern forming method according to [8] or [9], wherein, in the exposing, an electromagnetic wave having a wavelength of 15 nm or less is applied to the resist film.

[11] A The pattern forming method according to any one of [8] to [10], wherein a developing solution used in the developing comprises at least one selected from the group consisting of an ester compound, a ketone compound, and an alcohol compound.

Advantageous Effects of Invention

According to the present invention, a resist material capable of forming a resist film that is highly sensitive and enables high-resolution patterning can be obtained.

EMBODIMENTS OF CARRYING OUT THE INVENTION

Figure 1A:
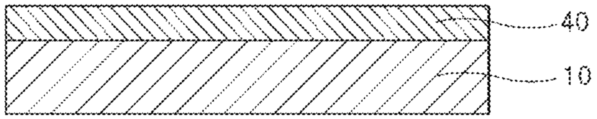
FIGS. 1A-1C is a cross-sectional view for illustrating an example of a structure composed of a substrate and a resist film.

The present invention is described in detail herein under. The description of the constitutive elements of the invention given herein under is for some typical embodiments and examples of the invention, but the invention should not be limited to such embodiments. In this description, the numerical range expressed by the wording "a number to another number" means the range that falls between the former number indicating the lower limit value of the range and the latter number indicating the upper limit value thereof.

Resist Material

The present invention relates to a resist material that comprises a polymer comprising a unit derived from a structure represented by the following formula (101):

[Formula 4]

Formula (101)

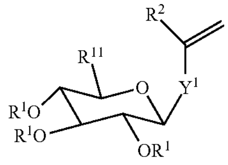

In the formula (101), $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent, and a plurality of $R^1$ may be the same or different. $R^{11}$ represents a hydrogen atom or an alkyl group optionally having a substituent. $R^2$ represents a hydrogen atom, an alkyl group, a fluorine atom, a chlorine atom, a bromine atom, or a halogenated alkyl group, and $Y^1$ represents a single bond or a linking group.

The resist material of the present invention comprises a polymer comprising a unit derived from the above-described structure, so that it can be used to form a highly sensitive resist film. Specifically, even in a case where the irradiation amount (dose amount) of electromagnetic radiations per unit area, which are applied to a resist film formed from the resist material, is small, a pattern having a desired shape can be formed. For example, with regard to the resist material of the present invention, even in a case where the dose amount is, for example, 250 $\mu C/cm^2$ or less upon electron beam irradiation, or further, even in a case where the dose amount is 200 $\mu C/cm^2$ or less or 160 $\mu C/cm^2$ or less, a pattern having a fine shape can be formed. In the case of a highly sensitive resist film, since the irradiation intensity of the electron beam can be reduced, and further, since the irradiation time can be shortened, the efficiency of a patterning step can be enhanced.

Furthermore, the resist material of the present invention comprises a polymer comprising a unit derived from the above-described structure, so that a resist film enabling high-resolution patterning can be formed. That is to say, a resist film formed from the resist material of the present invention has high resolution. For example, even in the case of a line pattern of a line-and-space pattern with a narrow line width, when the line is linear and there is no residue derived from the resist film in the space portion, it can be evaluated that the resist film has high resolution. That is, when the resolution of the resist film is high, a high-resolution pattern having a desired shape can be formed.

The content of the polymer is preferably 0.1% by mass or more, and more preferably 0.3% by mass or more, with respect to the total mass of the resist material. On the other hand, the content of the polymer is preferably 40% by mass or less, and more preferably 30% by mass or less, with respect to the total mass of the resist material.

The resist film formed from the resist material of the present invention is, for example, a film (a protective film) established on a substrate, in order to form a pattern on a substrate such as a silicon wafer. The resist film may be a film established on a substrate, so that it is allowed to directly come into contact with the substrate, or may also be a film laminated on a substrate via another layer. The resist film is processed into a pattern shape desired to be formed on a substrate, and a portion remaining as a pattern shape becomes a protective film in the subsequent etching step. Besides, after a pattern has been formed on a substrate, the resist film (protective film) may be removed from the substrate. Thus, the resist film is used in a step of forming a pattern on a substrate.

The resist material of the present invention is preferably a main-chain scission type positive-type resist material. The main chain of the polymer comprised in the resist material is cut by irradiation with electromagnetic radiations, and only the exposed portion is dissolved in a developing solution. Thereby, it becomes possible to form a higher resolution pattern.

<Polymer>

The resist material of the present invention comprises a polymer comprising a unit derived from a structure represented by a formula (101) shown below. Specifically, the polymer preferably comprises a unit derived from a sugar derivative. It is to be noted that, in the present description, the "unit" means a repeating unit (monomer unit) that constitutes the main chain of the polymer. However, there is also a case where the side chain of a unit derived from a single sugar derivative further comprises a unit derived from a sugar derivative. In this case, a repeating unit (monomer unit) constituting the polymer on the side chain also corresponds to the "unit" in the present description.

[Formula 5]

Formula (101)

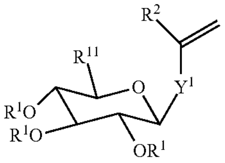

In the formula (101), $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent, and a plurality of $R^1$ may be the same or different. $R^{11}$ represents a hydrogen atom or an alkyl group optionally having a substituent. $R^2$ represents a hydrogen atom, an alkyl group, a fluorine atom, a chlorine atom, a bromine atom, or a halogenated alkyl group, and $Y^1$ represents a single bond or a linking group.

In the formula (101), $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent. Herein, the alkyl group optionally having a substituent includes a sugar derivative group, and $R^1$ may be a linear or branched sugar derivative-derived unit. The linear or branched sugar derivative-derived unit is preferably a sugar derivative having the same structure as that of a sugar derivative, to which it binds. Besides, when $R^1$ is a linear or branched sugar derivative-derived unit, the number of sugar derivative groups linked (the average polymerization degree of sugar derivatives) is preferably 20 or less, and more preferably 10 or less.

Among others, preferably, $R^1$ each independently represents a hydrogen atom, an alkyl group optionally having a substituent, or an acyl group optionally having a substituent; more preferably, $R^1$ each independently represents a hydrogen atom or an acyl group optionally having a substituent; and further preferably, $R^1$ each independently represents an acyl group optionally having a substituent. When $R^1$ is an acyl group optionally having a substituent, the sensitivity and resolution of the resist material can be more effectively enhanced.

When $R^1$ is an alkyl group or an acyl group, the number of carbon atoms contained in the alkyl or acyl group can be selected, as appropriate, depending on purpose. For example, the number of carbon atoms is preferably 1 or more, and is also preferably 200 or less, more preferably 100 or less, further preferably 20 or less, and particularly preferably 4 or less.

Specific examples of $R^1$ include: acyl groups such as an acetyl group, a propanoyl group, a butyryl group, an isobutyryl group, a valeryl group, an isovaleryl group, a pivaloyl group, a hexanoyl group, an octanoyl group, a chloroacetyl group, a trichloroacetyl group, a trifluoroacetyl group, a cyclopentanecarbonyl group, a cyclohexanecarbonyl group, a benzoyl group, a methoxybenzoyl group, a trifluoromethoxybenzoyl group, or a chlorobenzoyl group; and alkyl groups such as a methyl group, an ethyl group, an n-propyl group, an n-butyl group, an i-butyl group, or a t-butyl group. Among these groups, $R^1$ is preferably a methyl group, an ethyl group, an acetyl group, a propanoyl group, an n-butyryl group, an isobutyryl group, a benzoyl group, or a trimethylsilyl group, and $R^1$ is particularly preferably an acetyl group or a propanoyl group.

In the formula (101), $R^{11}$ represents a hydrogen atom or an alkyl group optionally having a substituent. When $R^1$ represents an alkyl group optionally having a substituent, examples of the alkyl group may include a methyl group, an ethyl group, and a propyl group. Among these, the alkyl group is preferably a methyl group, and it is preferable that such an alkyl group further has a substituent. Examples of the substituent possessed by the alkyl group may include a hydroxyl group, an acyl group, an allyl group, and an alkoxy group. Among these, the substituent is preferably a hydroxyl group or an acyl group. More specifically, when R represents an alkyl group optionally having a substituent, $R^{11}$ is preferably $—CH_2OR^1$, and examples of the $R^1$ may include the aforementioned groups. However, in the formula (101), $R^{11}$ is particularly preferably a hydrogen atom. By using a hydrogen atom as $R^{11}$, it becomes easy to form a fine pattern structure.

In the formula (101), $R^2$ represents a hydrogen atom, an alkyl group, a fluorine atom, a chlorine atom, a bromine atom, or a halogenated alkyl group. Among others, $R^2$ is preferably a hydrogen atom, an alkyl group containing 1 or more and 3 or less carbon atoms, a fluorine atom, a chlorine atom, or a bromine atom, and is particularly preferably a fluorine atom, a chlorine atom, or a bromine atom. By introducing a fluorine atom, a chlorine atom, or a bromine atom into $R^2$, a resist film having higher sensitivity can be formed.

In the formula (101), $Y^1$ each independently represents a single bond or a linking group. When $Y^1$ is a linking group, $Y^1$ may be a linking group containing no sugar units. Examples of the linking group may include an alkylene group, a phenylene group, and a group containing —O—, —C(═O)O—, etc. $Y^1$ may also be a linking group formed by combining these groups. Among others, $Y^1$ is preferably a linking group represented by any of the following structural formulae.

[Formula 6]

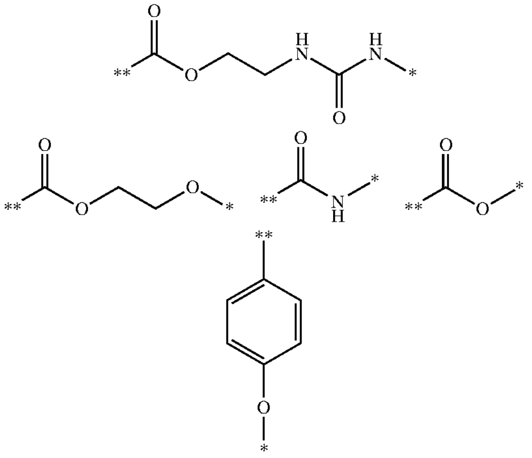

In the above structural formulae, the symbol ** represents a binding site with the main chain side, and the symbol * represents a binding site with the sugar unit on the side chain.

Besides, in the above formula (101), the structure of the sugar derivative is described as a cyclic structure. However, the structure of the sugar derivative may not only be a cyclic structure, but may also be a ring-opened structure (chain structure) called aldose or ketose.

Since the resist material of the present invention comprises the structure of a sugar derivative represented by the above formula (101), it is useful as a main-chain scission type positive-type resist material. In general, it is said that, in a main-chain scission type resist, radicals are generated in the polymer by light energy irradiated and the generated radicals cut the main chain. However, in the case of a conventional main-chain scission type resist, since radicals disappear after generation of the radicals, the efficiency of cutting the main chain is poor, and thus, the sensitivity is low. On the other hand, in the case of the resist material of the present invention, since the resist material has sugar chains having many C—O bonds, the sites of generating radicals are increased. Hence, even if the light energy per unit area is low, the frequency of generation of radicals is increased, so that the main chain scission can be promoted. It is considered that, thereby, the sensitivity of the resist material has been improved.

The content percentage (% by mass) of the unit derived from the structure represented by the formula (101) is preferably 1% by mass or more and 95% by mass or less, more preferably 3% by mass or more and 90% by mass or less, further preferably 7% by mass or more and 85% by mass or less, and particularly preferably 12% by mass or more and 80% by mass or less, with respect to the total mass of the polymer. By setting the content percentage of the unit derived from the structure represented by the formula (101) within the above-described range, the sensitivity and resolution of a resist film formed from the resist material can be more effectively enhanced.

The content percentage of the unit derived from the structure represented by the formula (101) can be obtained, for example, from $^1$H-NMR and the weight average molecular weight of the polymer. Specifically, the content percentage can be calculated using the following equation:

$$\text{Content percentage (\% by mass) of the unit derived from the structure represented by the formula (101)} = \text{mass of the unit derived from the structure represented by the formula (101)} \times \text{number of the units (monomers) derived from the structure represented by the formula (101)} / \text{weight average molecular weight of the polymer.}$$

It is preferable that the polymer comprised in the resist material of the present invention further comprises a unit derived from a structure represented by the following formula (102).

[Formula 7]

Formula (102)

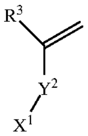

In the formula (102), $X^1$ represents an alkyl group optionally having a substituent, an acyl group optionally having a substituent, or an allyl group optionally having a substituent. $R^3$ represents a hydrogen atom, an alkyl group, a fluorine atom, a chlorine atom, a bromine atom, or a halogenated alkyl group, and $Y^2$ represents a single bond or a linking group.

In the formula (102), $X^1$ represents an alkyl group optionally having a substituent, an acyl group optionally having a substituent, or an allyl group optionally having a substituent, and preferably represents an alkyl group optionally having a substituent. The number of carbon atoms contained in the alkyl group is preferably 1 or more and 8 or less, more preferably 1 or more and 5 or less, and further preferably 1 or more and 3 or less. It is to be noted that the above-described number of carbon atoms means the number of carbon atoms excluding substituents. Examples of the alkyl group having a substituent may include —$CH_2$—OH, —$CH_2$—O-methyl, —$CH_2$—O-ethyl, —$CH_2$—O-n-propyl, —$CH_2$—O-isopropyl, —$CH_2$—O-n-butyl, —$CH_2$—O-isobutyl, —$CH_2$—O-t-butyl, —$CH_2$—O—(C═O)-methyl, —$CH_2$—O—(C═O)-ethyl, —$CH_2$—O—(C═O)-propyl, —$CH_2$—O—(C═O)-isopropyl, —$CH_2$—O—(C═O)-n-butyl, —$CH_2$—O—(C═O)-isobutyl, —$CH_2$—O—(C═O)-t-butyl, —$C_2H_4$—OH, —$C_2H_4$—O-methyl, —$C_2H_4$—O-ethyl, —$C_2H_4$—O-n-propyl, —$C_2H_4$—O-isopropyl, —$C_2H_4$—O-n-butyl, —$C_2H_4$—O-isobutyl, —$C_2H_4$—O-t-butyl, —$C_2H_4$—O—(C═O)-methyl, —$C_2H_4$—O—

(C═O)-ethyl, —$C_2H_4$—O—(C═O)-n-propyl, —$C_2H_4$—O—(C═O)-isopropyl, —$C_2H_4$—O—(C═O)-n-butyl, —$C_2H_4$—O—(C═O)-isobutyl, —$C_2H_4$—O—(C═O)-t-butyl, and —$C_2H_4$—O—(C═O)—$CH_2$—(C═O)-methyl. In addition, such an alkyl group having a substituent may also be a cycloalkyl group.

In the formula (102), $R^3$ represents a hydrogen atom, an alkyl group, a fluorine atom, a chlorine atom, a bromine atom, or a halogenated alkyl group. Among others, $R^3$ is preferably a hydrogen atom, an alkyl group containing 1 or more and 3 or less carbon atoms, a fluorine atom, a chlorine atom, or a bromine atom, and is particularly preferably a fluorine atom, a chlorine atom, or a bromine atom. By introducing a fluorine atom, a chlorine atom, or a bromine atom into $R^3$, a resist film having higher sensitivity can be formed. Besides, when the polymer comprised in the resist material further comprises the unit derived from the structure represented by the formula (102), at least either one of the $R^2$ in the formula (101) and $R^3$ in the formula (102) is preferably a fluorine atom, a chlorine atom, or a bromine atom. Otherwise, both of the $R^2$ in the formula (101) and $R^3$ in the formula (102) may be fluorine atoms, chlorine atoms, or bromine atoms.

In the formula (102), $Y^2$ represents a single bond or a linking group. When $Y^2$ is a linking group, examples of the $Y^2$ may include an alkylene group, a phenylene group, and a group containing —O—, —C(═O)O—, etc. $Y^2$ may also be a linking group formed by combining these groups. Among others, $Y^2$ is preferably a linking group represented by any of the following structural formulae.

[Formula 8]

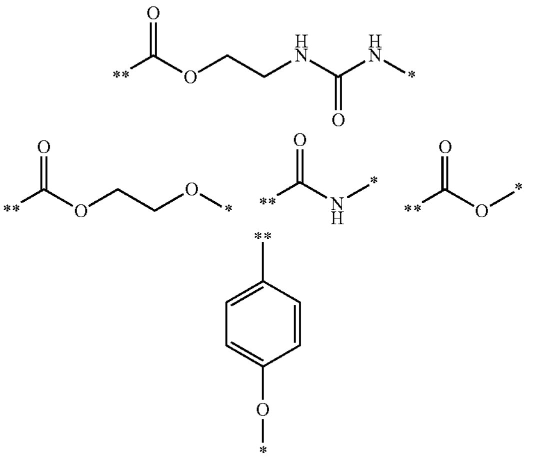

In the above structural formulae, the symbol ** represents a binding site with the main chain side, and the symbol * represents a binding site with $X^1$.

When the polymer comprises the unit derived from the structure represented by the formula (102), the content percentage (% by mass) of the unit derived from the structure represented by the formula (102) is preferably 1% by mass or more and 99% by mass or less, more preferably 3% by mass or more and 98% by mass or less, and particularly preferably 12% by mass or more and 97% by mass or less, with respect to the total mass of the polymer. Besides, the content percentage (% by mass) of the unit derived from the structure represented by the formula (102) can be calculated by the same method as the aforementioned calculation of the content percentage of the unit derived from the structure represented by the formula (101).

It is preferable that the polymer comprised in the resist material of the present invention further comprises a unit derived from a structure represented by the following formula (103). By allowing the polymer to further comprise the unit derived from the structure represented by the formula (103), the solubility into an organic solvent can be improved.

[Formula 9]

Formula (103)

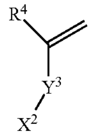

In the formula (103), $X^2$ represents an aryl group optionally having a substituent; $R^4$ represents a hydrogen atom, an alkyl group, a fluorine atom, a chlorine atom, a bromine atom, or a halogenated alkyl group; and $Y^3$ represents a single bond or a linking group.

In the formula (103), $X^2$ represents an aryl group optionally having a substituent. Among others, $X^2$ is preferably a phenyl group.

In the formula (103), $R^4$ represents a hydrogen atom, an alkyl group, a fluorine atom, a chlorine atom, a bromine atom, or a halogenated alkyl group. Among others, $R^4$ is preferably a hydrogen atom, an alkyl group containing 1 or more and 3 or less carbon atoms, a fluorine atom, a chlorine atom, or a bromine atom, and is particularly preferably a fluorine atom, a chlorine atom, or a bromine atom. By introducing a fluorine atom, a chlorine atom, or a bromine atom into $R^4$, a resist film having higher sensitivity can be formed.

In the formula (103), $Y^3$ represents a single bond or a linking group. When $Y^3$ is a linking group, examples of the $Y^3$ may include an alkylene group, a phenylene group, and a group containing —O—, —C(═O)O—, etc. $Y^3$ may also be a linking group formed by combining these groups. However, $Y^3$ is particularly preferably a single bond.

The unit derived from the structure represented by the formula (103) is preferably a unit derived from a styrene compound. Examples of the styrene compound may include styrene, o-methylstyrene, p-methylstyrene, ethylstyrene, p-methoxystyrene, p-phenylstyrene, 2,4-dimethylstyrene, p-n-octylstyrene, p-n-decylstyrene, p-n-dodecylstyrene, chlorostyrene, bromostyrene, trimethylsilylstyrene, hydroxystyrene, 3,4,5-methoxystyrene, pentamethyldisilylstyrene, t-butoxycarbonylstyrene, tetrahydropyranylstyrene, phenoxyethylstyrene, and t-butoxycarbonylmethylstyrene.

When the polymer comprises the unit derived from the structure represented by the formula (103), the content percentage (% by mass) of the unit derived from the structure represented by the formula (103) is preferably 1% by mass or more and 99% by mass or less, more preferably 3% by mass or more and 98% by mass or less, and particularly preferably 12% by mass or more and 97% by mass or less, with respect to the total mass of the polymer. It is to be noted that the content percentage (% by mass) of the unit derived from the structure represented by the formula (103) can be calculated by the same method as the aforementioned calculation of the content percentage of the unit derived from the structure represented by the formula (101).

The polymer comprised in the resist material of the present invention comprises the unit derived from the structure represented by the above-described formula (101), and preferably, further comprises the units derived from the structures represented by the formulae (102) and/or (103). When the polymer comprises the units derived from the structures represented by the formulae (102) and/or (103), the polymer becomes a copolymer. When the polymer is a copolymer, the copolymer may be either a block copolymer or a random copolymer. In addition, the copolymer may have a structure in which a part thereof is a random copolymer and another part thereof is a block copolymer. Thus, a suitable structure can be selected, as appropriate, depending on the intended use or required physical properties. However, the resist can have a high resolution as a result that radical-generating sites are dispersed in the polymer, and a fine pattern can be thereby formed. Accordingly, the copolymer is preferably a random copolymer.

The weight average molecular weight (Mw) of the polymer is preferably 5000 or more, more preferably 8000 or more, and further preferably 10000 or more. On the other hand, the weight average molecular weight (Mw) of the polymer is preferably 2,000,000 or less, more preferably 1,500,000 or less, further preferably 1,000,000 or less, and still further preferably 700,000 or less. Besides, the weight average molecular weight (Mw) of the polymer is a value measured relative to polystyrene according to GPC.

The ratio (Mw/Mn) between the weight average molecular weight (Mw) of the polymer and the number average molecular weight (Mn) of the polymer is preferably 1 or more. On the other hand, the Mw/Mn is preferably 100 or less, more preferably 50 or less, further preferably 20 or less, still further preferably 15 or less, and particularly preferably 10 or less.

The solubility of the polymer in at least one selected from PGMEA, PGME, THE, butyl acetate, anisole, cyclohexanone, ethyl lactate, N-methylpyrrolidone, γ-butyrolactone, and DMF is preferably 1% by mass or more, more preferably 2% by mass or more, particularly preferably 3% by mass or more, and further particularly preferably 4% by mass or more. The upper limit value of the solubility of the polymer in the above-described organic solvent is not particularly limited, and it can be set to be, for example, 40% by mass. Besides, the above-described solubility means the solubility of the polymer in at least any one selected from PGMEA, PGME, THE, butyl acetate, anisole, cyclohexanone, ethyl lactate, N-methylpyrrolidone, γ-butyrolactone, and DMF.

The method of measuring the solubility of the polymer comprises stirring a predetermined amount of polymer, while gradually adding PGMEA, PGME, THE, butyl acetate, anisole, cyclohexanone, ethyl lactate, N-methylpyrrolidone, γ-butyrolactone or DMF to the polymer, and then recording the amount of the added organic solvent when the polymer is dissolved in the organic solvent. For the stirring, a magnetic stirrer or the like may be used. Then, the solubility is calculated according to the following equation:

$$\text{Solubility (\% by mass)} = \text{mass of polymer}/(\text{mass of polymer} + \text{mass of organic solvent}) \times 100.$$

Synthesis Method of Polymer

The polymer can be synthesized by a known polymerization method such as living radical polymerization, living anionic polymerization, or atom transfer radical polymerization. For example, in the case of living radical polymerization, a copolymer can be obtained by reacting a monomer with a polymerization initiator such as AIBN (α,α'-azobisisobutyronitrile). In the case of living anionic polymerization, a polymer can be obtained by reacting butyllithium with a monomer in the presence of lithium chloride. In addition, in the Examples described herein, an example of synthesis using living anionic polymerization or living radical polymerization is shown, but the present invention is not limited thereto, and the synthesis can be appropriately performed by the above-described synthesis methods or known synthesis methods. For example, the method described in International Patent Publication WO99/062964 or the like can be used.

Moreover, upon the synthesis of the polymer, the synthesis may also be combined with a step of extracting a sugar moiety from lignocellulose or the like derived from woody plants or herbaceous plants. For example, when a method of extracting the sugar moiety from lignocellulose or the like derived from woody plants or herbaceous plants is adopted, the extraction method described in JP Patent Publication-A-2012-100546 A, etc. can be utilized.

In the case of xylan, it can be extracted by the method disclosed in, for example, JP Patent Publication-A-2012-180424 A.

In the case of cellulose, it can be extracted by the method disclosed in, for example, JP Patent Publication-A-2014-148629 A.

Then, upon the synthesis of the polymer, it is preferable that the sugar moiety obtained by the above-described extraction method is modified by esterification of the OH group thereof, and is then used. For example, when an acetyl group is introduced, the acetyl group is allowed to react with acetic anhydride, so that the acetylated sugar derivative moiety can be obtained.

Upon the synthesis of a copolymer, the copolymer can also be synthesized with reference to Macromolecules Vol. 36, No. 6, 2003. Specifically, each compound is added to a solvent including DMF, water or acetonitrile, and a reducing agent is then added thereto. The reducing agent may be, for example, $NaCNBH_3$. Thereafter, the obtained mixture is stirred at a temperature of 30° C. or higher and 100° C. or lower for 1 or more and 20 or less days, and a reducing agent is appropriately added to the reaction mixture, as necessary. A precipitate is obtained by adding water to the reaction mixture, and a solid is vacuum-dried to obtain a copolymer.

Examples of the method of synthesizing a copolymer include synthetic methods using radical polymerization, RAFT polymerization, ATRP polymerization, click reaction, or NMP polymerization, as well as the above-described method.

The radical polymerization is a polymerization reaction that occurs as a result of addition of an initiator to generate two free radicals by a thermal reaction or a photoreaction. Monomers (e.g., a styrene monomer and a sugar methacrylate compound formed by adding methacrylic acid to the β-1 position at the terminus of xylooligosaccharide) and an initiator (e.g., an azo compound such as azobisisobutyronitrile (AIBN)) are heated at 150° C., so that a polystyrene-polysaccharide methacrylate random copolymer can be synthesized.

The RAFT polymerization is a radical initiation polymerization reaction involving an exchange chain reaction utilizing a thiocarbonylthio group. For instance, there can be adopted a method comprising converting the OH group attached to position 1 at the terminus of xylooligosaccharide to a thiocarbonylthio group, and then allowing a styrene monomer to react with the resultant at a temperature of 30° C. or higher and 100° C. or lower to synthesize a copolymer (Material Matters, Vol. 5, No. 1, *Saishin Kobunshi Gosei* (Latest Polymer Synthesis), Sigma-Aldrich Japan).

In the ATRP polymerization, the OH group at the terminus of sugar is halogenated, and thereafter, a metal complex [(CuCl, $CuCl_2$, CuBr, $CuBr_2$, CuI, etc.)+TPMA (tris(2-pyridylmethyl)amine)], MeTREN (tris[2-(dimethylamino) ethyl]amine), etc.), a monomer (e.g., a styrene monomer), and a polymerization initiator (2,2,5-trimethyl-3-(1-phenylethoxy)-4-phenyl-3-azahexane) are allowed to react with the sugar, so that a sugar copolymer (e.g., a sugar-styrene block copolymer) can be synthesized.

In the NMP polymerization, an alkoxy amine derivative used as an initiator is heated, so that it is subjected to a coupling reaction with a monomer molecule so as to generate nitroxide. Thereafter, radicals are generated as a result of thermal dissociation, so that the polymerization reaction progresses. Such an NMP polymerization is one type of living radical polymerization reaction. Monomers (e.g., a styrene monomer and a sugar methacrylate compound formed by adding methacrylic acid to the β-1 position at the terminus of xylooligosaccharide) are mixed, and 2,2,6,6-tetramethylpiperidine 1-oxyl (TEMPO) is used as an initiator. The mixture is heated at 140° C., so that a polystyrene-polysaccharide methacrylate random copolymer can be synthesized.

The click reaction is a 1,3-dipolar azide/alkyne cycloaddition reaction of using sugar having a propargyl group and a Cu catalyst.

<Organic Solvent>

The resist material of the present invention may further comprise an organic solvent. However, the present resist material may further comprise water or an aqueous solvent such as various types of solutions, in addition to such an organic solvent. Examples of the organic solvent may include an alcohol-based solvent, an ether-based solvent, a ketone-based solvent, a sulfur-based solvent, an amide-based solvent, an ester-based solvent, and a hydrocarbon-based solvent. These solvents may be used alone or in combination of two or more types.

Examples of an alcohol solvent include: methanol, ethanol, n-propanol, i-propanol, n-butanol, i-butanol, sec-butanol, tert-butanol, n-pentanol, i-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, cyclohexanol, phenol, methylcyclohexanol, 3,3,5-trimethylcyclohexanol, benzyl alcohol, and diacetone alcohol; ethylene glycol, 1,2-propylene glycol, 1,3-butyleneglycol, 2,4-pentanediol, 2-methyl-2,4-pentanediol, 2,5-hexanediol, 2,4-heptanediol, 2-ethyl-1,3-hexanediol, diethylene glycol, dipropyleneglycol, triethylene glycol, tripropylene glycol, 1H,1H-trifluoroethanol, 1H,1H-pentafluoropropanol, and 6-(perfluoroethyl)hexanol.

In addition, examples of a partially etherified polyhydric alcohol solvent include ethylene glycol monomethyl ether, ethylene glycol monoethyl ether, ethylene glycol monopropyl ether, ethylene glycolmonobutyl ether, ethylene glycol monohexyl ether, ethylene glycolmonophenyl ether, ethylene glycol mono-2-ethylbutyl ether, diethyleneglycol monomethyl ether, diethylene glycol monoethyl ether, diethyleneglycol monopropyl ether, diethyleneglycol monobutyl ether, diethyleneglycol monohexyl ether, diethylene glycol dimethyl ether, diethylene glycol ethyl methyl ether, propylene glycol monomethyl ether(PGME), propylene glycol monoethyl ether, propylene glycol monopropylether, propylene glycol monobutyl ether, dipropylene glycol monomethylether, dipropylene glycol monoethyl ether, and dipropylene glycolmonopropyl ether.

Examples of an ether solvent include diethyl ether, dipropyl ether, dibutyl ether, diphenyl ether, and tetrahydrofuran (THF).

Examples of a ketone solvent include acetone, methyl ethyl ketone, methyl-n-propyl ketone, methyl-n-butyl ketone, diethyl ketone, methyl-1-butyl ketone, methyl-n-pentyl ketone, ethyl-n-butyl ketone, methyl-n-hexyl ketone, di-i-butyl ketone, trimethylnonanone, cyclopentanone, cyclohexanone, cycloheptanone, cyclooctanone, methylcyclohexanone, 2,4-pentanedione, acetonylacetone, acetophenone, and furfural.

Examples of a sulfur-containing solvent include dimethyl sulfoxide.

Examples of an amide-based solvent include N,N'-dimethylimidazolidinone, N-methylformamide, N,N-dimethylformamide, N,N-diethylformamide, acetamide, N-methylacetamide, N,N-dimethylacetamide, N-methylpropionamide, and N-methylpyrrolidone.

Examples of an ester solvent include diethyl carbonate, propylenecarbonate, methyl acetate, ethyl acetate, .gamma.-butyrolactone, .gamma.-valerolactone, n-propyl acetate, i-propyl acetate, n-butylacetate, i-butyl acetate, sec-butyl acetate, n-pentyl acetate, sec-pentylacetate, 3-methoxybutyl acetate, methylpentyl acetate, 2-ethylbutylacetate, 2-ethylhexyl acetate, benzyl acetate, cyclohexyl acetate, methylcyclohexyl acetate, n-nonyl acetate, methyl acetoacetate, ethylacetoacetate, ethylene glycol monomethyl ether acetate, ethylene glycolmonoethyl ether acetate, diethylene glycol monomethyl ether acetate, diethylene glycol monoethyl ether acetate, diethylene glycol mono-n-butylether acetate, propylene glycol monomethyl ether acetate (PGMEA), propylene glycol monoethyl ether acetate, propylene glycol monopropyl ether acetate, propylene glycol monobutyl ether acetate, dipropyleneglycol monomethyl ether acetate, dipropylene glycol monoethyl etheracetate, glycol diacetate, methoxytriglycol acetate, ethyl propionate, n-butyl propionate, i-amyl propionate, methyl 3-methoxy propionate, diethyl oxalate, di-n-butyl oxalate, methyl lactate, ethyl lactate, n-butyl lactate, n-amyl lactate, diethyl malonate, dimethyl phthalate, and diethyl phthalate.

Examples of a hydrocarbon solvent include: aliphatic hydrocarbonsolvents such as n-pentane, i-pentane, n-hexane, i-hexane, n-heptane, i-heptane, 2,2,4-trimethyl pentane, n-octane, i-octane, cyclohexane, andmethylcyclohexane; and aromatic hydrocarbon solvents such as benzene, toluene, xylene, mesitylene, ethylbenzene, trimethylbenzene, methylethylbenzene, n-propylbenzene, i-propylbenzene, diethylbenzene, i-butylbenzene, triethylbenzene, di-i-propylbenzene, n-amyl naphthalene, and anisole.

Of these, propylene glycol monomethyl ether acetate (PGMEA), N,N-dimethylformamide (DMF), propylene glycol monomethyl ether (PGME), anisole, ethanol, methanol, acetone, methyl ethyl ketone, hexane, tetrahydrofuran (THF), dimethyl sulfoxide (DMSO), 1H,1H-trifluoroethanol, 1H,1H-pentafluoropropanol, 6-(perfluoroethyl) hexanol, ethyl acetate, propyl acetate, butyl acetate, cyclohexanone, furfural, N-methylpyrrolidone, or .gamma.-butyrolactone are preferable, PGMEA, PGME, THE, butyl acetate, anisole, cyclohexanone, N-methylpyrrolidone, .gamma.-butyrolactone, or DMF is more preferable, anisole, PGME or PGMEA is even more preferable. These solvents may be used eithersingly or in combination of two or more types.

The content of the organic solvent is preferably 10% by mass or more, more preferably 20% by mass or more, and even more preferably 30% by mass or more with respect to the total mass of the resist material. Moreover, the content of the organic solvent is preferably 99.9% by mass or less, and more preferably 99% by mass or less. By setting the content of the organic solvent within the above range, the coatability of the resist material can be improved.

<Optional Components>

The resist material of the present invention may comprise optional components as described below.

<<Monomeric Components>>

The resist material of the present invention may comprise monomeric components that constitute the polymer, in addition to the polymer. Examples of the monomeric component may include a compound represented by the aforementioned formula (101), and compounds represented by the aforementioned formulae (102) and/or (103).

<<Crosslinkable Compound>>

The resist material of the present invention may further comprise a crosslinkable compound. Because of this crosslinking reaction, the formed resist film becomes strong, and etching resistance can be enhanced. In addition, when such a crosslinkable compound is added to the resist material, the crosslinking reaction of the polymer in an exposed portion can be promoted by irradiation with an electromagnetic wave, so that the resist material can be insolubilized. In this case, the resist film (resist material) in the unexposed portion can be eliminated by treating it with an appropriate developing solution.

The crosslinkable compound is not particularly limited, and a crosslinkable compound having at least two crosslink-forming substituents is preferably used. A compound having two or more, for example, 2 to 6 crosslink-forming substituents of at least one type, which are selected from an isocyanate group, an epoxy group, a hydroxymethylamino group, and an alkoxymethylamino group, can be used as a crosslinkable compound. As such a crosslinkable compound, only one type of compound can be used, or a combination of two or more types of compounds can also be used.

These crosslinkable compounds are able to cause a crosslinking reaction due to self-condensation. Moreover, these crosslinkable compounds are also able to cause a crosslinking reaction with constitutional units comprised in the polymer.

<<Catalyst>>

To the present resist material, an acid compound, such as p-toluenesulfonic acid, trifluoromethanesulfonic acid, pyridinium-p-toluenesulfonic acid, salicylic acid, sulfosalicylic acid, citric acid, benzoic acid, ammonium dodecylbenzenesulfonate, or hydroxybenzoic acid, can be added as a catalyst for promoting a crosslinking reaction. Moreover, as such catalyst, an acid generator, such as 2,4,4,6-tetrabromocyclohexadienone, benzoin tosylate, 2-nitrobenzyl tosylate, bis (4-tert-butylphenyl) iodonium triluoromethanesulfonate, triphenylsulfonium triluoromethanesulfonate, phenyl-bis (trichloromethyl)-s-triazine, benzoin tosylate, or N-hydroxysuccinimide trifluoromethanesulfonate, can be added.

<<Light Reflection Preventing Agent>>

The resist material of the present invention may further contain a light antireflection agent. As a light antireflection agent, for example, a light-absorbing compound can be mentioned. Examples of a light-absorbing compound may include those having high light-absorbing ability in the photosensitive characteristic wavelength region of a photosensitive component in a photoresist provided on the anti-light-reflection film such as a benzophenone compound, a benzotriazole compound, an azo compound, a naphthalene compound, an anthracene compound, an anthraquinone compound, and a triazine compound. Examples of a polymer may include poly ester, polyimide, polystyrene, novolacresin, polyacetal, and acrylic polymer. Examples of a polymer having a light-absorbing group linked by a chemical bond include a polymer having a light-absorbing aromatic ring structure such as an anthracene ring, anaphthalene ring, a benzene ring, a quinoline ring, a quinoxaline ring, or a thiazole ring.

<<Other Components>>

The resist material may further contain anionic liquid, a surfactant, and the like. By incorporating an ionic liquid in the resist material, the compatibility between a resist and an organic solvent can be increased. By including a surfactant in the resist material, the coatability of the resist material on a substrate can be improved. Further, when forming a pattern using the resist material, it is possible to improve coatability of a resist composition or the like applied subsequently to the resist material. Examples of a preferable surfactant include a nonionic surfactant, a fluorine surfactant, and a silicone surfactant. In addition, any known material such as a rheology modifier and an adhesion aid may be included in the resist material.

The content of the optional component as described above is preferably 10% by mass or less, and more preferably 5% by mass or less with respect to the total mass of the resist material.

(Resist Film)

The present invention may relate to a resist film formed from the aforementioned resist material. The resist film is used when a pattern is formed on a substrate or the like, and is a film capable of functioning as a protective film when an etching treatment is performed on the substrate. Besides, the resist film includes either a layered film before the formation of a pattern, or an intermittent film after the formation of a pattern.

Figure 1B:
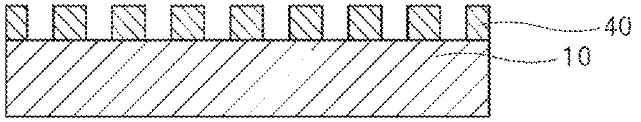
Figure 1C:
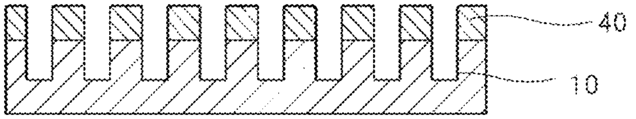

FIG. 1(*a*) shows a laminate, in which a resist film 40 is formed on a substrate 10. Besides, although it is not shown in the FIGURE, another layer may be established between the substrate 10 and the resist film 40.

As shown in FIG. 1(*b*), at least a portion of the resist film 40 is removed, so that a desired pattern shape can be formed on the substrate 10. For example, exposure and development treatments are performed on the resist film 40, so that a pattern shape as shown in FIG. 1(*b*) can be formed.

In the exposure step, an electromagnetic wave is applied to the resist film 40 through a mask on which a circuit pattern is drawn, so that a portion of the resist film, to which the light has been applied, is changed in properties, and a pattern is transcribed. At this time, in the portion to which the light has been applied, the main chain of the polymer comprised in the resist film is preferably cut. Thereby, the molecular weight of the polymer is reduced, and the portion to which the light is applied can be dissolved in a developing solution and can be then removed, and as a result, an intermittent portion of the resist film is formed. In the thus formed intermittent portion of the resist film, the substrate 10 is exposed. Using chlorine gas, or boron trichloride, methane tetrafluoride gas, methane trifluoride gas, ethane hexafluoride gas, propane octafluoride gas, butane octafluoride gas, sulfur hexafluoride gas, argon gas, oxygen gas, helium gas, etc., reactive ion etching or the like is carried out with inductively coupled plasma, etc., on the exposed substrate 10, and a pattern is thereby formed, so that a pattern as shown in FIG. 1(*c*) can be formed on the substrate 10. In addition, in the exposure step, exposure without using masks can also be carried out using a maskless exposure machine or a maskless electron beam lithography system. In such a case, light energy is applied to the resist film 40 using a fine beam, so that a latent image can be directly drawn on the resist.

The thickness of the resist film can be adjusted, as appropriate, depending on intended use, and it is, for example, 1 nm or more and 20000 nm or less, more preferably 1 nm or more and 10000 nm or less, further preferably 1 nm or more and 5000 nm or less, and particularly preferably 1 nm or more and 3000 nm or less.

The resist film may be either a film into which a metal is to be introduced, or a film into which a metal has been introduced. Besides, the resist film may comprise a metal. In this case, the content percentage of the metal in the resist film is preferably 3 at % or more, more preferably 5 at % or more, further preferably 7 at % or more, and particularly preferably 10 at % or more. The content percentage of the metal can be calculated, for example, by the following method. The resist film after introduction of the metal is subjected to EDX analysis (energy dispersive X-ray spectroscopy) using the electronic microscope JSM7800F (manufactured by JEOL, Ltd.), so as to calculate the ratio of the metal component (the content percentage of the metal), which is defined as the content percentage of the metal.

Pattern Forming Method

The present invention also relates to a pattern forming method using the aforementioned resist material. Specifically, the pattern forming method preferably comprises a step of applying the aforementioned resist material onto a substrate to form a resist film, an exposure step, and a development step.

Examples of the substrate used in the pattern forming method may include substrates made of glass, silicon, SiN, GaN, AlN, $SiO_2$, quartz, sapphire, etc. Otherwise, a substrate consisting of an organic material such as PET, PE, PEO, PS, a cycloolefin polymer, polylactic acid, or a cellulose nanofiber may also be used.

Before application of the resist material onto the substrate, a step of washing the substrate is preferably established. By washing the surface of the substrate, the coatability of the resist material is improved. As a washing method, a conventionally known method can be utilized, and examples of the known method may include an oxygen plasma treatment, an ozone oxidation treatment, an acid alkali treatment, and a chemical modification treatment.

The method of applying the resist material onto the substrate is not particularly limited, and for example, according to a known method such as a spin-coating method, the resist material can be applied onto the substrate. Moreover, after the resist material has been applied onto the substrate, the substrate may be heated, so that the resist material may be hardened to form a resist film. The temperature applied upon the heating of the coated film is not particularly limited, and it is preferably 60° C. or higher and 550° C. or lower. Moreover, the heating treatment is preferably carried out under the ambient atmosphere and at a relatively low temperature.

The substrate and the resist film are preferably laminated in this order, such that the adjacent layers are allowed to directly come into contact with each other. However, another layer may be established between individual layers. For example, an anchor layer or an antireflective film may be established between the substrate and the resist film. The anchor layer is a layer that controls the wettability of the substrate and enhances the adhesiveness between the substrate and the resist film. The antireflective film is a layer that absorbs the used electromagnetic wave. Moreover, a plurality of layers consisting of different materials may be sandwiched between the substrate and the resist film. These materials are not particularly specified, and examples of the materials may include inorganic materials such as $SiO_2$, SiN, $Al_2O_3$, AlN, GaN, GaAs, W, Cr, Ru, TaN, SOG or amorphous carbon, and organic materials such as commercially available SOC or adhesives. In a case where an antireflective film is established between the substrate and the resist film, a composition for antireflective films that is used in the formation of the antireflective film is not particularly limited, and a composition can be arbitrarily selected from those commonly used in the lithographic process, and can be then used.

When a pattern is formed on the resist film, the pattern forming method preferably comprises a step of applying an electromagnetic wave to the resist film through a mask on which a circuit pattern is drawn (exposure step) or a step of applying a fine electromagnetic wave to the resist film without using such a mask (exposure step). As an electromagnetic wave used in the exposure, a KrF excimer laser (wavelength: 248 nm), an ArF excimer laser (wavelength: 193 nm), an F2 excimer laser (wavelength: 157 nm), an electron beam, EUV (extreme ultraviolet, wavelength: 13.5 nm or less), etc. can be used. Since a fine pattern is drawn by the exposure, an electron beam or EUV is preferably used. After completion of the exposure, post exposure baking can be carried out, as necessary. Such post exposure baking is preferably carried out under conditions of a heating temperature of 70° C. to 150° C. and a heating time of 0.3 to 10 minutes.

In the exposure step, an electromagnetic wave is applied to the resist film, so that a portion of the resist film, to which the light has been applied, is changed in properties, and a pattern on the mask is transcribed. At this time, in the portion to which the light has been applied, the main chain of the polymer comprised in the resist film is preferably cut. In the portion in which the main chain of the polymer has been cut, in the subsequent development step, the resist film (resist material) in the exposed portion is to be eliminated.

When an electromagnetic wave is applied to the resist film in the exposure step, the wavelength of the electromagnetic wave is preferably 15 nm or less. On the other hand, the wavelength of the electromagnetic wave is preferably 0.0001 nm or more. In the exposure step, by applying an electromagnetic wave having a wavelength of 15 nm or less to the resist film, a fine pattern can be formed with high accuracy.

Besides, when the resist material comprises a polymer having a crosslinkable group, or when a crosslinkable compound is added to the resist material, the crosslinking reaction of the polymer in an exposed portion can be promoted by applying light energy to the resist material, so that the resist material can be insolubilized. In this case, the resist film (resist material) in the unexposed portion can be eliminated by treating it with an appropriate developing solution.

The developing solution used in the development step is not particularly limited, and a known developing solution can be used. Examples of the developing solution may include: aqueous solutions of aromatic compounds such as xylene, toluene or anisole, esters such as pentyl acetate, hexyl acetate, heptyl acetate, octyl acetate, ethyl acetate, propyl acetate, n-butyl acetate, ethyl lactate, propyl lactate, butyl lactate or γ-butyrolactone, alcohols such as ethanol or isopropanol, ketones such as diethyl ketone, methyl ethyl ketone, methyl isobutyl ketone or cyclohexanone, ethers such as diethylene glycol dimethyl ether, organic acids such as acetic anhydride or acetic acid, and alkali metal hydroxides such as potassium hydroxide or sodium hydroxide; aqueous solutions of quaternary ammonium hydroxide such as tetramethylammonium hydroxide, tetraethylammonium hydroxide or choline; and alkaline aqueous solutions including amine aqueous solutions such as ethanolamine, propylamine or ethylenediamine. As a developing solution, the aforementioned aqueous solutions can be used alone, or in combination of two or more types. Furthermore, a surfactant and the like can also be added to these developing solutions. Developing conditions are appropriately selected from a temperature of −70° C. to 50° C. and a developing time of 10 to 300 seconds.

The developing solution used in the development step preferably comprises at least one selected from the group consisting of an ester compound, a ketone compound, and an alcohol compound. By using such a developing solution, it becomes possible to perform highly sensitive and high-resolution patterning. Besides, a combination of two or more types of the aforementioned compounds may be used in the developing solution. When the aforementioned compounds are mixed with one another in the developing solution, examples of the developing solution that can be used herein may include a mixed solution of two or more types of ester compounds such as butyl acetate, a mixed solution of an ester compound and an alcohol compound such as isopropyl alcohol, a mixed solution of an ester compound and a ketone compound such as cyclohexanone, a mixed solution of an ester compound and an ether compound such as diethylene glycol dimethyl ether, a mixed solution of two or more types of ketone compounds, a mixed solution of a ketone compound and an alcohol compound, a mixed solution of a ketone compound and an ester compound, a mixed solution of two or more types of alcohol compounds, a mixed solution of an alcohol compound and an organic acid such as acetic anhydride, and a mixed solution of an alcohol compound and an amine compound such as tetramethylammonium hydroxide.

In addition, after completion of the development step, a rinsing step of using a rinsing solution may be established. The rinsing solution is not particularly limited, and a known rinsing solution can be used. For example, xylene, butyl acetate, ethanol, isopropyl alcohol, methyl isobutyl ketone, pure water, etc. can be used. As such a rinsing solution, the aforementioned substances can be used each alone, or in a combination of two or more types. Moreover, a surfactant and the like may be added to such a rinsing solution, and may be then used. Conditions applied in the rinsing step are selected, as appropriate, from a temperature of −70° C. to 50° C. and a rinsing time of 10 to 100 seconds.

The pattern forming method of the present invention may further comprise a metal introduction step before the development step. That is to say, the pattern forming method of the present invention may further comprise a metal introduction step between the step of forming a resist film and the exposure step, or after the development step. In this case, the metal introduction step may be a step of introducing a metal into a resist film, such as an SIS method (Sequential Infiltration Synthesis). Examples of the metal to be introduced into the resist film may include Li, Be, Na, Mg, Al, Si, K, Ca, Sc, Ti, V, Cr, Mn, Fe, Co, Ni, Cu, Zn, Ga, Ge, As, Rb, Sr, Y, Zr, Nb, Mo, Ru, Pd, Ag, Cd, In, Sn, Sb, Te, Cs, Ba, La, Hf, Ta, W, Re, Os, Ir, Pt, Au, Hg, Tl, Pb, Bi, Po, Ce, Pr, Nd, Pm, Sm, Eu, Gd, Tb, Dy, Ho, Er, Tm, Yb, and Lu. Such a process can be carried out according the method described, for example, in Journal of Photopolymer Science and Technology, Volume 29, Number 5 (2016) 653-657. Moreover, in the metal introduction step, a method using a metal complex gas, a method of applying a solution containing a metal onto the resist film, or a method of introducing a metal into the resist according to an ion implantation technique can be adopted.

The pattern forming method of the present invention is a method of forming a pattern on a resist film formed from a resist material, and it may further comprise a step of processing a semiconductor substrate, etc., using the pattern formed on the resist film as a protective film. Such a step is referred to as an etching step. In this case, the etching step is established as a post step of the development step.

Examples of the method of processing a semiconductor substrate in the etching step may include known methods including: reactive ion etching (RIE) such as chemical dry etching, and physical etching such as chemical wet etching (wet development), sputter etching, or ion beam etching. The processing of a semiconductor substrate is preferably carried out by dry etching using gas such as, for example, tetrafluoromethane, perfluorocyclobutane ($C_4F_8$), perfluoropropane ($C_3F_8$), trifluoromethane, carbon monoxide, argon, oxygen, nitrogen, chlorine, sulfur hexafluoride, difluoromethane, nitrogen trifluoride, and chlorine trifluoride.

EXAMPLES

Hereinafter, the features of the present invention will be described more specifically with reference to Examples and Comparative Examples. The materials, used amounts, proportions, treatment content, treatment procedures, and the like shown in the following Examples can be appropriately changed to the extent that such changes do not depart from the spirit of the present invention. Therefore, the scope of the present invention should not be construed as being limited by the following specific examples.

[Example 1: Synthesis of Copolymer 1]

(Synthesis of Acetyl Sugar Methacrylate 1)

20 g of Xylose was added to a mixed solution of 250 g of acetic anhydride and 320 g of acetic acid, and the obtained solution was then stirred at 30° C. for 2 hours. Approximately five times amount of cold water was slowly added to the reaction solution while stirring, and the obtained mixture was then stirred for 2 hours. Thereafter, the reaction mixture was left at rest overnight, so that a crystal was precipitated to obtain 25 g of acetyl sugar. The acetyl sugar (10 g) was added to a solution prepared by adding 1.2 g of ethylenediamine and 0.14 g of acetic acid to 400 mL of THE in a flask and setting the temperature at 0° C., and the obtained mixture was then stirred for 4 hours. This reaction mixture was poured into 1 L of cold water, and was then extracted with dichloromethane twice. The obtained extract (20 g), 300 mL of dichloromethane and 4.8 g of triethylamine were added into a flask, and were then cooled to −30° C. Thereafter, 2.8 g of methacryloyl chloride was added to the reaction mixture, and the thus obtained mixture was then stirred for 2 hours. The obtained reaction mixture was poured into 300 mL of cold water, and was the extracted with dichloromethane twice, and thereafter, the solvent was concentrated to obtain 16.1 g of acetyl sugar methacrylate 1. The structure of the obtained acetyl sugar methacrylate 1 is as follows.

[Formula 10]

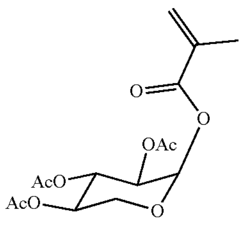

(Synthesis of acetyl sugar methacrylate 1—methyl chloroacrylate Random Copolymer)

14.8 g of Acetyl sugar methacrylate 1, 60 g of methyl 2-chloroacrylate (manufactured by Tokyo Chemical Industry Co., Ltd.), 100 g of THE used as a solvent THF, and 0.5 g of azobis(isobutyronitrile) used as a polymerization initiator were placed into a flask, and the flask was then hermetically sealed, followed by nitrogen substitution. Under a nitrogen atmosphere, the temperature was increased to 78° C., and the mixture was then stirred for 6 hours. Thereafter, the temperature was returned to room temperature, and the inside of the flask was set to ambient atmosphere. To the obtained solution, 300 g of methanol was added dropwise, so as to precipitate a polymer. Thereafter, a solution containing the precipitated polymer was subjected to suction filtration to obtain 10 g of white copolymer 1. Individual constituent units of the obtained copolymer 1 have the following structures.

[Formula 11]

Unit (A)

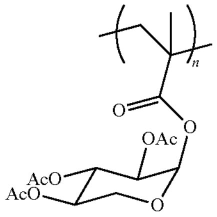

Unit (B)

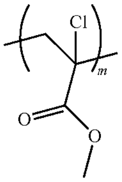

wherein n=105 and m=105.

[Example 2: Synthesis of Copolymer 2]

(Synthesis of acetyl sugar methacrylate 1—methyl chloroacrylate—styrene Random Copolymer)

11.4 g of Acetyl sugar methacrylate 1, 4.0 g of methyl 2-chloroacrylate (manufactured by Tokyo Chemical Industry Co., Ltd.), 4.6 g of styrene (manufactured by Tokyo Chemical Industry Co., Ltd.), 100 g of THE used as a solvent THE, and 0.8 g of azobis(isobutyronitrile) used as a polymerization initiator were placed into a flask, and the flask was then hermetically sealed, followed by nitrogen substitution. Under a nitrogen atmosphere, the temperature was increased to 78° C., and the mixture was then stirred for 6.0 hours. Thereafter, the temperature was returned to room temperature, and the inside of the flask was set to ambient atmosphere. To the obtained solution, 300 g of methanol was added dropwise, so as to precipitate a polymer. Thereafter, a solution containing the precipitated polymer was subjected to suction filtration to obtain 11 g of white copolymer 2. Individual constituent units of the obtained copolymer 2 have the following structures.

[Formula 12]

Unit (A)

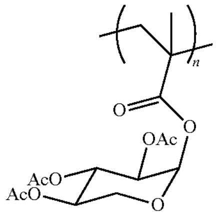

Unit (B)

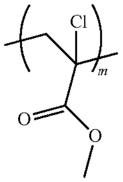

Unit (C)

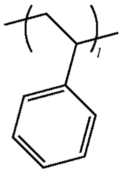

wherein n=84, m=84, and l=112.

[Example 3: Synthesis of Copolymer 3]

(Synthesis of acetyl sugar methacrylate 1—methyl chloroacrylate—benzyl methacrylate Random Copolymer)

10.4 g of Copolymer 3 was obtained by the same method as the synthesis of copolymer 2, with the exceptions that the additive amount of acetyl sugar methacrylate 1 was changed to 12.5 g, that the additive amount of methyl chloroacrylate was changed to 4.3 g, and further that 4.6 g of styrene was changed to 3.2 g of benzyl methacrylate (manufactured by Tokyo Chemical Industry Co., Ltd.). Individual constituent units of the obtained copolymer 3 have the following structures.

[Formula 13]

Unit (A)

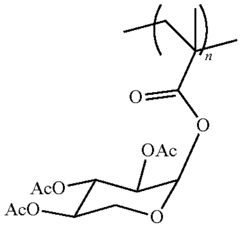

-continued

Unit (B)

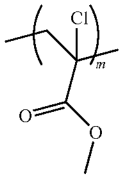

Unit (C)

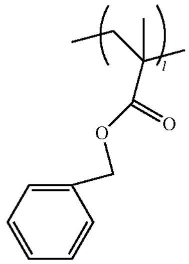

wherein n=100, m=100, and l=50.

[Example 4: Synthesis of Copolymer 4]

(Synthesis of acetyl sugar methacrylate 1—methyl chloroacrylate—α-methylstyrene Random Copolymer)

12 g of Copolymer 4 was obtained by the same method as the synthesis of copolymer 2, with the exceptions that the additive amount of acetyl sugar methacrylate 1 was changed to 12.4 g, that the additive amount of methyl chloroacrylate was changed to 4.2 g, and further that 4.6 g of styrene was changed to 3.6 g of α-methylstyrene. Individual constituent units of the obtained copolymer 4 have the following structures.

[Formula 14]

Unit (A)

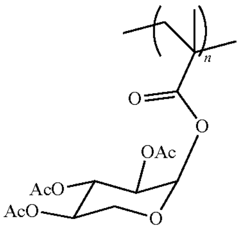

Unit (B)

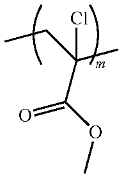

Unit (C)

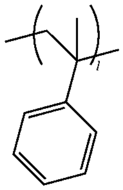

wherein n=91, m=91, and l=78.

[Example 5: Synthesis of Copolymer 5]

(Synthesis of Sugar Methacrylate)

33 g of Xylose was dissolved in 150 mL of water, and 28.5 g each of ammonium hydrogen carbonate (manufactured by Wako Pure Chemical Industries, Ltd.) was added to the obtained solution four times every 24 hours. The obtained mixture was stirred at 37° C. for 96 hours. Thereafter. 200 mL of distilled water was added to the reaction mixture, and water was then distilled away until the volume of the reaction mixture became 20 mL. Thereafter, 150 ml of water was added to the mixture, and the thus obtained mixture was then concentrated to a volume of 10 mL. This operation was repeatedly carried out until ammonia odor disappeared, and the resultant was then freeze-dried to obtain a white solid. This substance was dissolved in 50 mL of $1\times10^{-3}$ M KOH aqueous solution, and 10.4 g of 2-isocyanatoethyl methacrylate (manufactured by Wako Pure Chemical Industries, Ltd.) was then added to the obtained solution. The obtained mixture was intensively stirred for 12 hours, while the temperature was kept at 3° C. Thereafter, the precipitated white solid was removed, and the filtrate was then washed using 50 mL of diethyl ether 4 times, followed by freeze-drying. After that, the obtained white solid was dissolved in a mixed solution of 2 mL of water and 10 mL of methanol, and the obtained solution was then added dropwise to a mixed solution comprising 200 mL of acetone, followed by cooling. Thereafter, the resultant was filtered and was then dried under reduced pressure to obtain 25 g of sugar methacrylate. The structure of the sugar methacrylate is as follows.

[Formula 15]

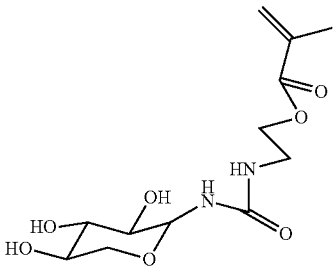

(Synthesis of sugar methacrylate—methyl chloroacrylate—α-methylstyrene Random Copolymer)

10.0 g of Copolymer 5 was obtained by the same method as the synthesis of copolymer 2, with the exceptions that 11.4 g of acetyl sugar methacrylate 1 was changed to 7.8 g of sugar methacrylate, that the additive amount of methyl chloroacrylate was changed to 6.2 g, and further that 4.6 g of styrene was changed to 3.2 g of α-methylstyrene. Individual constituent units of the obtained copolymer 5 have the following structures.

[Formula 16]

Unit (A)

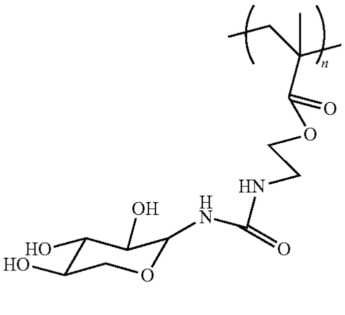

-continued

Unit (B)

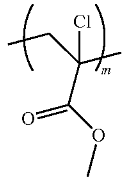

Unit (C)

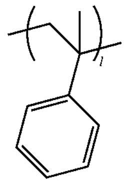

wherein n=48, m=96, and l=96.

[Example 6: Synthesis of Copolymer 6]

(Synthesis of Acetyl Sugar Methacrylate 2)

120 g of Acetic anhydride was reacted with 10 g of sugar methacrylate for 2 hours. Thereafter, the reaction was terminated with 33% by mass of magnesium acetate solution, and pure water was then added to the reaction solution to precipitate a crystal, so as to obtain acetyl sugar methacrylate 2. The structure of the obtained acetyl sugar methacrylate 2 is as follows.

[Formula 17]

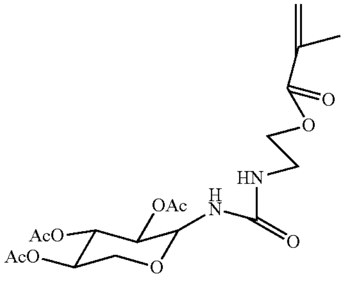

(Synthesis of Acetyl Sugar Methacrylate 2—Methyl Chloroacrylate—α-Methylstyrene Random Copolymer 11.5 g of Copolymer 6 was obtained by the same method as the synthesis of copolymer 2, with the exceptions that 11.4 g of acetyl sugar methacrylate 1 was changed to 12.2 g of acetyl sugar methacrylate 2, and that 4.6 g of styrene was changed to 3.2 g of α-methylstyrene. Individual constituent units of the obtained copolymer 6 have the following structures.

[Formula 18]

Unit (A)

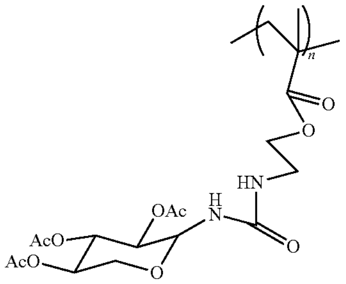

-continued

Unit (B)

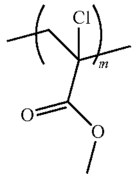

Unit (C)

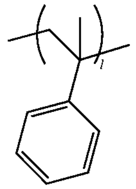

wherein n=77, m=77, and l=66.

[Example 7: Synthesis of Copolymer 7]

(Synthesis of Acetyl Sugar Methacrylate 1—Methyl Acrylate—α-Methylstyrene Random Copolymer)

12.0 g of Copolymer 7 was obtained by the same method as the synthesis of copolymer 2, with the exceptions that the additive amount of acetyl sugar methacrylate 1 was changed to 13.0 g, that 4.0 g of methyl chloroacrylate was changed to 3.2 g of methyl acrylate, and further that 4.6 g of styrene was changed to 3.8 g of α-methylstyrene. Individual constituent units of the obtained copolymer 7 have the following structures.

[Formula 19]

Unit (A)

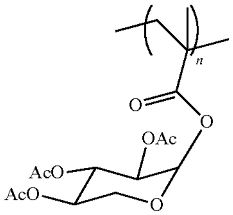

Unit (B)

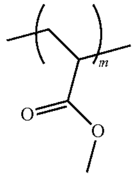

Unit (C)

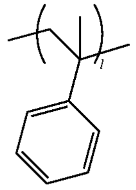

wherein n=98, m=98, and l=84.

[Example 8: Synthesis of Copolymer 8]

(Synthesis of Acetyl Xylooligosaccharide Methacrylate)

30.0 g of Acetyl xylooligosaccharide methacrylate was obtained by the same method as the synthesis of acetyl sugar methacrylate 1, with the exception that 20 g of xylose was changed to 55 g of xylooligosaccharide (average sugar chain length: 3). The obtained acetyl xylooligosaccharide methacrylate is as follows.

[Formula 20]

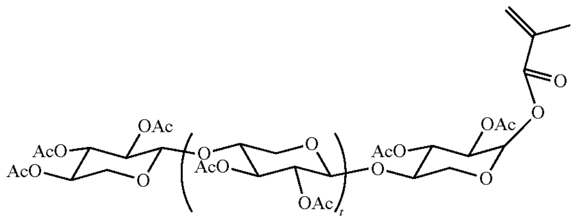

wherein t=1.

(Synthesis of Acetyl Xylooligosaccharide Methacrylate—Methyl Chloroacrylate—α-Methylstyrene Random Copolymer)

8.8 g of Copolymer 8 was obtained by the same method as the synthesis of copolymer 2, with the exceptions that 11.4 g of acetyl sugar methacrylate 1 was changed to 8.4 g of acetyl xylooligosaccharide methacrylate, that the additive amount of methyl chloroacrylate was changed to 5.2 g, and that 4.6 g of styrene was changed to 6.4 g of α-methylstyrene. Individual constituent units of the obtained copolymer 8 have the following structures.

[Formula 21]

Unit (A)

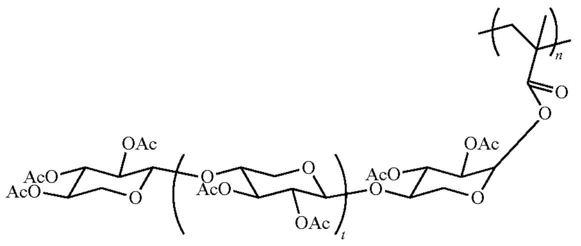

Unit (B)

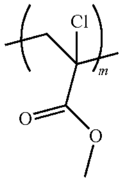

Unit (C)

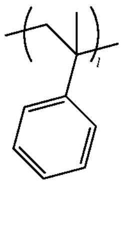

wherein t=1, n=30, m=120, and l=150.

[Example 9: Synthesis of Copolymer 9]

(Acetyl Sugar Chloroacrylate)

20 g of Acetyl sugar chloroacrylate was obtained by the same synthesis as the synthesis of acetyl sugar methacrylate 1, with the exception that methacryloyl chloride was changed to 2-chloroacrylic acid chloride (manufactured by 1Click Chemistry Stock Products). The structure of the obtained acetyl sugar chloroacrylate is as follows.

[Formula 22]

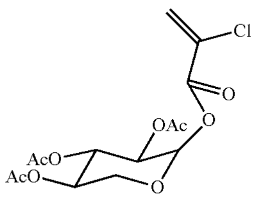

(Synthesis of Acetyl Sugar Chloroacrylate—Methyl Chloroacrylate—α-Methylstyrene Random Copolymer)

11.2 g of Copolymer 9 was obtained by the same method as the synthesis of copolymer 2, with the exceptions that 11.4 g of acetyl sugar methacrylate 1 was changed to 14.1 g of acetyl sugar chloroacrylate, that the additive amount of methyl chloroacrylate was changed to 4.1 g, and that 4.6 g of styrene was changed to 3.5 g of α-methylstyrene. Individual constituent units of the obtained copolymer 9 have the following structures.

[Formula 23]

Unit (A)

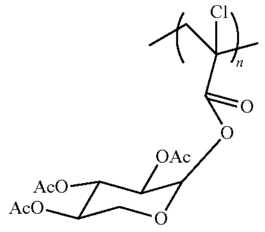

Unit (B)

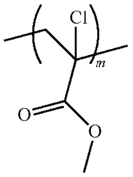

Unit (C)

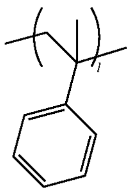

wherein n=91, m=91, and l=78.

[Example 10: Synthesis of Copolymer 10]

(Synthesis of Acetyl Sugar Methacrylate 1—Methyl Chloroacrylate—3,5-bis(trifluoromethyl)styrene Random Copolymer 10.1 g of Copolymer 10 was obtained by the same method as the synthesis of copolymer 2, with the exceptions that the additive amount of acetyl sugar methacrylate 1 was changed to 10.0 g, that the additive amount of methyl chloroacrylate was changed to 3.5 g, and that 4.6 g of styrene was changed to 7.0 g of 3,5-bis(trifluoromethyl)styrene (manufactured by Tokyo Chemical Industry Co., Ltd.). Individual constituent units of the obtained copolymer 10 have the following structures.

[Formula 24]

Unit (A)

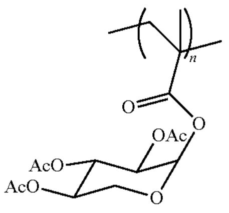

Unit (B)

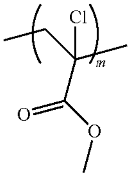

Unit (C)

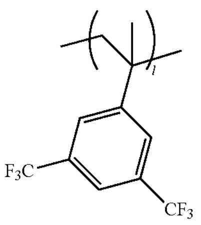

wherein n=98, m=84, and l=98.

[Example 11: Synthesis of Copolymer 11]

(Synthesis of Acetyl Sugar Methacrylate 3)

22.0 g of Acetyl sugar methacrylate 3 was obtained by the same method as the synthesis of acetyl sugar methacrylate 1, with the exception that 20 g of xylose was changed to 21 g of glucose (manufactured by Tokyo Chemical Industry Co., Ltd.). The obtained acetyl sugar methacrylate 3 is as follows.

[Formula 25]

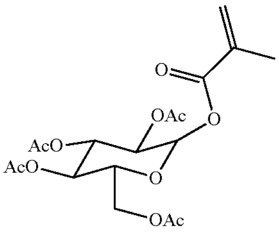

(Synthesis of Acetyl Sugar Methacrylate 3—Methyl Chloroacrylate—α-Methylstyrene Random Copolymer)

8.5 g of Copolymer 11 was obtained by the same method as the synthesis of copolymer 2, with the exceptions that 11.41 g of acetyl sugar methacrylate 1 was changed to 15.0 g of acetyl sugar methacrylate 3, that the additive amount of methyl chloroacrylate was changed to 2.5 g, and that 4.6 g of styrene was changed to 2.5 g of α-methylstyrene. Individual constituent units of the obtained copolymer 11 have the following structures.

[Formula 26]

Unit (A)

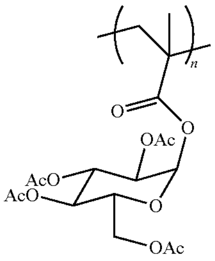

Unit (B)

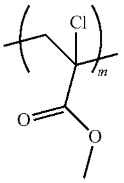

Unit (C)

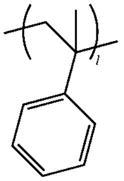

wherein n=110, m=55, and l=55.

[Example 12: Synthesis of Copolymer 12]

(Synthesis of Acetyl Sugar Styrene)

Acetyl sugar was synthesized in the same manner as the synthesis of acetyl sugar methacrylate 1. Subsequently, 10.8 g (90 mmol) of 4-vinylphenol, 32.2 g (32 mmol) of acetyl sugar, and 0.5 g of zinc chloride were heated in a silicon oil bath at 160° C. for 30 minutes, while stirring. The melted mixture was cooled to approximately 60° C., and was then dissolved in 200 mL of benzene. The obtained solution was washed with water twice, and was then washed with 1 M sodium hydroxide until the water phase became almost colorless. Subsequently, the resultant was washed with water twice, and was then dried, followed by concentration under reduced pressure, to obtain 26.5 g of acetyl sugar styrene. The structure of the obtained acetyl sugar styrene is as follows.

[Formula 27]

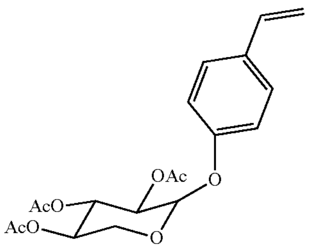

(Synthesis of Acetyl Sugar Styrene—Methyl Chloroacrylate—α-Methylstyrene Random Copolymer)

13.1 g of Copolymer 12 was obtained by the same method as the synthesis of copolymer 2, with the exceptions that 11.4 g of acetyl sugar methacrylate 1 was changed to 8.6 g of acetyl sugar styrene, that the additive amount of methyl chloroacrylate was changed to 5.7 g, and further that 4.6 g of styrene was changed to 5.6 g of α-methylstyrene. Individual constituent units of the obtained copolymer 12 have the following structures.

[Formula 28]

Unit (A)

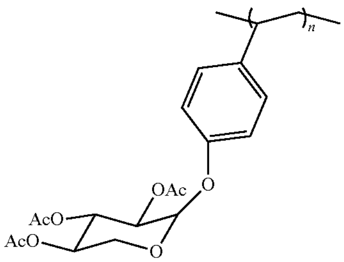

Unit (B)

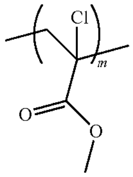

Unit (C)

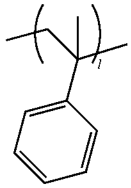

wherein n=66, m=132, and l=132.

[Example 13: Synthesis of Copolymer 13]

(Synthesis of Acetyl Sugar Methacrylate 1—Methyl Chloroacrylate—α-Methylstyrene Random Copolymer)

10.1 g of Copolymer 13 was obtained by the same method as the synthesis of copolymer 2, with the exceptions that the additive amount of acetyl sugar methacrylate 1 was changed to 16.3 g, that the additive amount of methyl chloroacrylate was changed to 1.9 g, and that 4.6 g of styrene was changed to 1.9 g of α-methylstyrene. Individual constituent units of the obtained copolymer 13 have the following structures.

[Formula 29]

Unit (A)

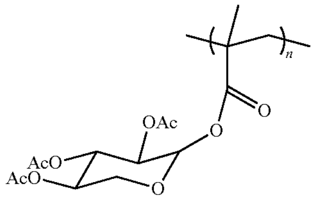

Unit (B)

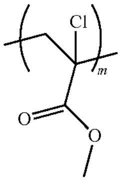

-continued

Unit (C)

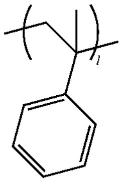

wherein n=120, m=40, and l=40.

[Comparative Example 1: Synthesis of Copolymer 14]

(Synthesis of Methyl Chloroacrylate—α-Methylstyrene Random Copolymer)

13.1 g of Copolymer 14 was obtained by the same method as the synthesis of copolymer 1, with the exceptions that 14.8 g of acetyl sugar methacrylate 1 was changed to 10.1 g of α-methylstyrene, and that the additive amount of methyl chloroacrylate was changed to 9.9 g. Individual constituent units of the obtained copolymer 14 have the following structures.

[Formula 30]

Unit (B)

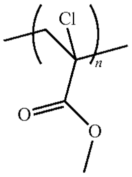

Unit (C)

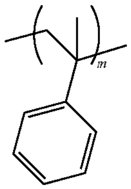

wherein n=225 and m=225.

[Comparative Example 2: Synthesis of copolymer 15]

(Synthesis of Methyl Chloroacrylate—Benzyl Methacrylate Random Copolymer)

10.1 g of Copolymer 15 was obtained by the same method as the synthesis of copolymer 1, with the exceptions that 14.8 g of acetyl sugar methacrylate 1 was changed to 8.1 g of benzyl methacrylate, and that the additive amount of methyl chloroacrylate was changed to 11.9 g. Individual constituent units of the obtained copolymer 15 have the following structures.

[Formula 31]

Unit (B)

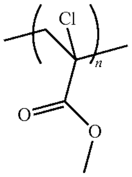

-continued

Unit (C)

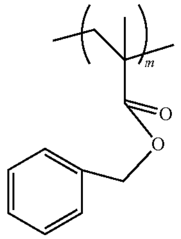

wherein n=175 and m=175.

[Comparative Example 3: Synthesis of Copolymer 16]

(Synthesis of 1—Adamantyl Methacrylate—Methyl Chloroacrylate—Benzyl Methacrylate Random Copolymer)

Copolymer 16 was obtained by the same method as the synthesis of copolymer 2, with the exceptions that 12.1 g of acetyl sugar methacrylate 1 was changed to 10.0 g of 1-adamantyl methacrylate (manufactured by Tokyo Chemical Industry Co., Ltd.), that the additive amount of methyl chloroacrylate was changed to 5.4 g, and that the additive amount of α-methylstyrene that was 3.6 g was changed to 4.6 g. Individual constituent units of the obtained copolymer 16 have the following structures.

[Formula 32]

Unit (A)

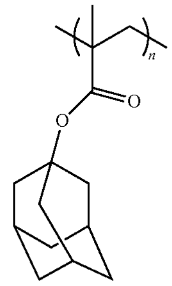

-continued

Unit (B)

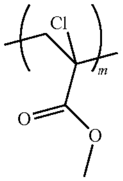

Unit (C)

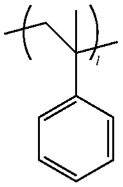

wherein n=105, m=105, and l=90.

[Analysis of Copolymers]

<Weight Average Molecular Weight>

The weight average molecular weight of each copolymer was measured by a gel permeation chromatography (GPC) method.

GPC column: Shodex K-806M/K-802 coupled column (manufactured by SHOWA DENKO K. K.)

Column temperature: 40° C.

Mobile phase: chloroform

Detector: R1

After completion of all of the polymerizations, the polymerization degrees thereof were measured by the GPC method, so that it was confirmed that random copolymers each having a desired polymerization degree and a desired average molecular weight could be synthesized. It is to be noted that the weight average molecular weight Mw of each copolymer was 50,000.

<Ratio of Unit (a): Unit (b): Unit (c)>

The ratio (molar ratio) of the unit (a): unit (b):unit (c) of each copolymer was obtained and calculated according to $^{1}$H-NMR. The molar ratio indicates the ratio regarding the number of each unit present in the copolymer.

TABLE 1

| | | Unit (A) | Unit (B) | Unit (C) | Ratio (mol %) |
|---|---|---|---|---|---|
| Ex. 1 | Copolymer 1 | Acetyl sugar methacrylate 1 | Methyl chloroacrylate | | 50:50:0 |
| Ex. 2 | Copolymer 2 | Acetyl sugar methacrylate 1 | Methyl chloroacrylate | Styrene | 30:30:40 |
| Ex. 3 | Copolymer 3 | Acetyl sugar methacrylate 1 | Methyl chloroacrylate | Benzyl methacrylate | 40:40:20 |
| Ex. 4 | Copolymer 4 | Acetyl sugar methacrylate 1 | Methyl chloroacrylate | α-Methylstyrene | 35:35:30 |
| Ex. 5 | Copolymer 5 | Sugar methacrylate | Methyl chloroacrylate | α-Methylstyrene | 20:40:40 |
| Ex. 6 | Copolymer 6 | Acetyl sugar methacrylate 2 | Methyl chloroacrylate | α-Methylstyrene | 35:35:30 |
| Ex. 7 | Copolymer 7 | Acetyl sugar methacrylate 1 | Methyl acrylate | α-Methylstyrene | 35:35:30 |
| Ex. 8 | Copolymer 8 | Acetyl xylooligosaccharide methacrylate | Methyl chloroacrylate | α-Methylstyrene | 10:40:50 |
| Ex. 9 | Copolymer 9 | Acetyl sugar chloroacrylate | Methyl chloroacrylate | α-Methylstyrene | 35:35:30 |
| Ex. 10 | Copolymer 10 | Acetyl sugar methacrylate 1 | Methyl chloroacrylate | 3,5-Bis(trifluoromethyl)styrene | 35:30:30 |
| Ex. 11 | Copolymer 11 | Acetyl sugar methacrylate 3 | Methyl chloroacrylate | α-Methylstyrene | 50:25:25 |
| Ex. 12 | Copolymer 12 | Acetyl sugar styrene | Methyl chloroacrylate | α-Methylstyrene | 20:40:40 |
| Ex. 13 | Copolymer 13 | Acetyl sugar methacrylate 1 | Methyl chloroacrylate | α-Methylstyrene | 60:20:20 |
| Comp. Ex. 1 | Copolymer 14 | — | Methyl chloroacrylate | α-Methylstyrene | 0:50:50 |
| Comp. Ex. 2 | Copolymer 15 | — | Methyl chloroacrylate | Benzyl methacrylate | 0:50:50 |
| Comp. Ex. 3 | Copolymer 16 | 1-Adamantyl methacrylate | Methyl chloroacrylate | α-Methylstyrene | 35:35:30 |

[Evaluation of Solubility of Copolymer]

The synthesized copolymers were weighed, and were then dissolved in anisole (manufactured by Tokyo Chemical Industry Co., Ltd.) at 23° C. to each result in 2.5% by mass. Thereafter, the solubility was confirmed by visual observation, and the solubility was evaluated according to the following criteria.

○: The solution is transparent, and neither cloudiness nor precipitate is found.

Δ: The solution is clouded, but no precipitate is found.

x: A precipitate is found in the solution.

[Production of Sample for Use in Resist Evaluation]

The synthesized copolymers were weighed, and were then dissolved in anisole (manufactured by Tokyo Chemical Industry Co., Ltd.) at 23° C. to each result in 3.0% by mass. The obtained solution was spin-coated onto a silicon wafer to a film thickness of 100 nm, and was then heated on a hot plate at 180° C. for 2 minutes for baking. After completion of the baking, electron beam irradiation was performed on the silicon wafer using the electron beam drawing device ELS-F125 (manufactured by ELIONIX INC.) under conditions of an acceleration voltage of 50 kV and an electric current of 500 pA (wavelength of 0.0053 nm), so that a latent image was drawn. Thereafter, the below-mentioned steps were carried out to produce a sample for use in evaluation of sensitivity and resolution, and the sensitivity and resolution were then evaluated.

[Evaluation of Sensitivity]

The dose amount was set to be 60 $\mu C/cm^2$, 160 $\mu C/cm^2$, or 260 $\mu C/cm^2$, and a latent image having a line width of 100 nm and a line:space ratio of 1:1 was drawn on the resist film. After the drawing of the latent image, the silicon wafer was immersed in pentyl acetate (manufactured by Tokyo Chemical Industry Co., Ltd.) at 23° C. for developing. After completion of the developing, the silicon wafer was dried by nitrogen blowing to produce a sample for use in evaluation of sensitivity.

The surface and the cross section of the line-and space portion were observed using the scanning electron microscope (SEM) JSM7800F (manufactured by JEOL Ltd.) under conditions of an acceleration voltage of 5 kV, an emission electric current of 86.0 μA, and a magnification of 100,000-fold, so that the sensitivity was confirmed. The states were evaluated according to the following evaluation criteria. It is to be noted that when a line-and-space pattern was developed at a dose amount of 160 $\mu C/cm^2$ or less, the sensitivity was evaluated to be favorable.

○: A line-and-space pattern is developed.

x: A line-and-space pattern is not developed.

[Evaluation of Resolution]

The dose amount was set to be 200 $\mu C/cm^2$, and a latent image having a line width of 20 nm, 50 nm or 100 nm, and a line:space ratio of 1:1 was drawn on the resist film. After the drawing of the latent image, the silicon wafer was immersed in pentyl acetate (manufactured by Tokyo Chemical Industry Co., Ltd.) at 23° C. for developing. After completion of the developing, the silicon wafer was dried by nitrogen blowing to produce a sample for use in evaluation of resolution.

Subsequently, the surface and the cross section of the line-and space portion were observed using the scanning electron microscope (SEM) JSM7800F (manufactured by JEOL Ltd.) under conditions of an acceleration voltage of 5 kV, an emission electric current of 86.0 μA, and a magnification of 100,000-fold, so that the resolution was confirmed. The states were evaluated according to the following evaluation criteria. It is to be noted that a state, in which a line pattern was linear in a line-and-space with a line width of 50 nm or less and there was no residue derived from the resist film in the space portion, was evaluated to be favorable.

○: A line pattern in the line-and-space is linear, and there is no residue derived from the resist film in the space portion.

x: A line pattern in the line-and-space is not linear (is meandering), or there is a residue derived from the resist film in the space portion, or a line pattern cannot be confirmed.

TABLE 2

| | | Solubility 2.5 mass % | Sensitivity (dose: μC/cm) | | | Resolution (line width) | | | |
|---|---|---|---|---|---|---|---|---|---|
| | | concentration | 60 | 160 | 260 | 15 nm | 20 nm | 50 nm | 100 nm |
| Ex. 1 | Copolymer 1 | Δ | x | ○ | ○ | x | ○ | ○ | ○ |
| Ex. 2 | Copolymer 2 | ○ | ○ | ○ | ○ | x | ○ | ○ | ○ |
| Ex. 3 | Copolymer 3 | ○ | ○ | ○ | ○ | x | ○ | ○ | ○ |
| Ex. 4 | Copolymer 4 | ○ | ○ | ○ | ○ | ○ | ○ | ○ | ○ |
| Ex. 5 | Copolymer 5 | Δ | ○ | ○ | ○ | x | ○ | ○ | ○ |
| Ex. 6 | Copolymer 6 | ○ | ○ | ○ | ○ | x | x | ○ | ○ |
| Ex. 7 | Copolymer 7 | ○ | x | ○ | ○ | x | ○ | ○ | ○ |
| Ex. 8 | Copolymer 8 | ○ | ○ | ○ | ○ | x | x | ○ | ○ |
| Ex. 9 | Copolymer 9 | ○ | ○ | ○ | ○ | ○ | ○ | ○ | ○ |
| Ex. 10 | Copolymer 10 | ○ | ○ | ○ | ○ | x | ○ | ○ | ○ |
| Ex. 11 | Copolymer 11 | ○ | ○ | ○ | ○ | x | ○ | ○ | ○ |
| Ex. 12 | Copolymer 12 | ○ | ○ | ○ | ○ | x | ○ | ○ | ○ |
| Ex. 13 | Copolymer 13 | ○ | ○ | ○ | ○ | ○ | ○ | ○ | ○ |
| Comp. Ex. 1 | Copolymer 14 | ○ | x | x | ○ | ○ | ○ | ○ | ○ |
| Comp. Ex. 2 | Copolymer 15 | ○ | x | x | x | x | x | ○ | ○ |
| Comp. Ex. 3 | Copolymer 16 | ○ | x | x | x | x | x | x | ○ |

When resist films were formed using the copolymers obtained in the Examples, the obtained resist films had high sensitivity, and high-resolution patterns were formed.

REFERENCE SIGNS LIST

10 SUBSTRATE
40 RESIST FILM

The invention claimed is:

1. A monomer for forming resist material represented by the following formula (101):

Formula (101)

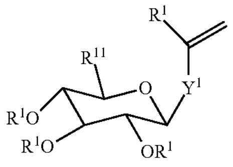

wherein $R^1$ each independently represents a hydrogen atom, an alkyl group optionally having a substituent, an acyl group optionally having a substituent, an allyl group optionally having a substituent, an alkoxy group optionally having a substituent, or an alkylsilyl group optionally having a substituent, and a plurality of $R^1$ may be the same or different; $R^{11}$ represents a hydrogen atom or an alkyl group optionally having a substituent; $R^2$ represents a fluorine atom, a chlorine atom, or a bromine atom; and $Y^1$ represents a single bond or a linking group.

2. The monomer for forming resist material according to claim 1, wherein, in the formula (101), $R^1$ is an acyl group optionally having a substituent.

3. The monomer for forming resist material according to claim 1, wherein, in the formula (101), $R^{11}$ is a hydrogen atom.

* * * * *